United States Patent
Kurrus (10) Patent No.: US 8,292,907 B2
(45) Date of Patent: Oct. 23, 2012

(54) BALLOON ASSISTED OCCLUSION DEVICE

(75) Inventor: Michael R. Kurrus, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 964 days.

(21) Appl. No.: 11/848,777

(22) Filed: Aug. 31, 2007

(65) Prior Publication Data

US 2009/0062836 A1    Mar. 5, 2009

(51) Int. Cl.
*A61B 17/08* (2006.01)
(52) U.S. Cl. ............... 606/157; 606/194; 606/213
(58) Field of Classification Search .............. 623/2.11, 623/1.21; 604/101.01, 101.03, 101.05; 128/831, 128/843, 887
See application file for complete search history.

(56) References Cited

U.S. PATENT DOCUMENTS

| | | | | |
|---|---|---|---|---|
| 4,573,966 | A | * | 3/1986 | Weikl et al. ............ 604/509 |
| 4,836,204 | A | * | 6/1989 | Landymore et al. ....... 606/215 |
| 4,911,163 | A | | 3/1990 | Fina |
| 5,167,614 | A | | 12/1992 | Tessmann et al. |
| 5,167,628 | A | | 12/1992 | Boyles |
| 5,176,692 | A | | 1/1993 | Wilk et al. |
| 5,188,595 | A | * | 2/1993 | Jacobi ................... 604/509 |
| 5,192,301 | A | | 3/1993 | Kamiya et al. |
| 5,275,826 | A | * | 1/1994 | Badylak et al. .......... 424/551 |
| 5,486,195 | A | | 1/1996 | Myers et al. |
| 5,591,197 | A | | 1/1997 | Orth et al. |
| 5,634,936 | A | | 6/1997 | Linden et al. |
| 5,702,421 | A | | 12/1997 | Schneidt |
| 5,749,922 | A | * | 5/1998 | Slepian et al. .......... 29/469.5 |
| 5,766,219 | A | | 6/1998 | Horton |
| 5,772,632 | A | * | 6/1998 | Forman ................. 604/103.01 |
| 5,861,003 | A | | 1/1999 | Latson et al. |
| 5,899,917 | A | * | 5/1999 | Edwards et al. .......... 606/195 |
| 5,976,174 | A | | 11/1999 | Ruiz |
| 6,063,112 | A | * | 5/2000 | Sgro .................... 623/1.12 |
| 6,238,416 | B1 | | 5/2001 | Sideris |
| 6,270,524 | B1 | | 8/2001 | Kim |
| 6,296,657 | B1 | | 10/2001 | Brucker |
| 6,517,573 | B1 | | 2/2003 | Pollock et al. |
| 6,692,458 | B2 | | 2/2004 | Forman et al. |
| 6,949,116 | B2 | | 9/2005 | Solymar et al. |
| 6,994,092 | B2 | | 2/2006 | van der Burg et al. |
| 7,128,073 | B1 | | 10/2006 | van der Burg et al. |
| 7,165,552 | B2 | | 1/2007 | Deem et al. |

(Continued)

FOREIGN PATENT DOCUMENTS

JP          02-307480          12/1990

*Primary Examiner* — Ryan Severson
*Assistant Examiner* — David Eastwood
(74) *Attorney, Agent, or Firm* — Brinks Hofer Gilson & Lione (57) ABSTRACT

A vascular occlusion device for occluding a body cavity. The device includes an elongate member having an inflation lumen, an occlusion lumen, and a first portion extending distally from a proximal end and a second portion extending distally from the first portion to the distal end. An inflatable proximal balloon is disposed about the first portion and an inflatable distal balloon is disposed about the second portion. The inflation lumen is configured to inflate at least one of the balloons. The occlusion lumen is configured to introduce an occlusive material into the body cavity by way of an occlusion port located between the two balloons to occlude the body cavity. In some examples, the body cavity includes a patent foramen ovale.

15 Claims, 5 Drawing Sheets

U.S. PATENT DOCUMENTS

| | | |
|---|---|---|
| 7,591,268 B2 | 9/2009 | Lowe et al. |
| 2002/0029051 A1 | 3/2002 | Callister et al. |
| 2002/0072763 A1* | 6/2002 | Chien et al. ................... 606/194 |
| 2002/0082685 A1 | 6/2002 | Sirhan et al. |
| 2002/0151968 A1 | 10/2002 | Zilla et al. |
| 2003/0029457 A1 | 2/2003 | Callister et al. |
| 2003/0045860 A1* | 3/2003 | Leu ............................... 604/509 |
| 2003/0051735 A1 | 3/2003 | Pavcnik et al. |
| 2003/0130713 A1* | 7/2003 | Stewart et al. ................ 607/119 |
| 2003/0229366 A1 | 12/2003 | Reggie et al. |
| 2004/0024419 A1* | 2/2004 | Slepian et al. ................ 606/214 |
| 2004/0186561 A1 | 9/2004 | McGuckin et al. |
| 2004/0220596 A1 | 11/2004 | Frazier et al. |
| 2004/0260340 A1 | 12/2004 | Jacobs et al. |
| 2004/0267191 A1 | 12/2004 | Gifford, III et al. |
| 2005/0010248 A1 | 1/2005 | Lafontaine et al. |
| 2005/0034735 A1 | 2/2005 | Deem et al. |
| 2005/0085770 A1* | 4/2005 | Don Michael ........... 604/101.03 |
| 2005/0149173 A1 | 7/2005 | Hunter et al. |
| 2005/0149175 A1 | 7/2005 | Hunter et al. |
| 2005/0177103 A1* | 8/2005 | Hunter et al. .............. 604/96.01 |
| 2005/0192626 A1 | 9/2005 | Widomski et al. |
| 2005/0209633 A1 | 9/2005 | Callister et al. |
| 2005/0251201 A1 | 11/2005 | Roue et al. |
| 2005/0256532 A1 | 11/2005 | Nayak et al. |
| 2006/0009798 A1 | 1/2006 | Callister et al. |
| 2006/0105015 A1* | 5/2006 | Perla et al. .................... 424/423 |
| 2006/0106418 A1 | 5/2006 | Seibold et al. |
| 2006/0212055 A1 | 9/2006 | Karabey et al. |
| 2006/0235467 A1 | 10/2006 | DeVore |
| 2007/0014870 A1* | 1/2007 | Matheny ....................... 424/551 |

* cited by examiner

BALLOON ASSISTED OCCLUSION DEVICE

BACKGROUND

1. Field of the Invention

The present invention generally relates to vascular occlusion devices. More specifically, the invention relates to a vascular occlusion device for closing an atrial septal defect.

2. Description of Related Art

A number of different devices may be used to occlude a body cavity including, for example, a blood vessel. When it is desirable to quickly occlude a blood vessel, an inflatable balloon may be used. However, balloons have the disadvantage of being temporary. Another example of an occlusion device includes embolization coils. Embolization coils are permanent and promote blood clots or tissue growth over a period of time, thereby occluding the body cavity. However, while the blood clots or the tissue grows, blood may continue to flow past the coil and through the body cavity. It may take a significant period of time for sufficient tissue to grow to fully occlude the body cavity. This leaves a patient open to a risk of injury from the condition which requires the body cavity be occluded. An example of such a condition includes, but is not limited to, an atrial septal defect such as a patent foramen ovale.

In view of the above, it is apparent that there exists a need for an improved vascular occlusion device.

SUMMARY

In satisfying the above need, as well as overcoming the enumerated drawbacks and other limitations of the related art, the present invention provides a vascular occlusion device for occluding a body cavity. The device includes an elongate member extending from a proximal end to a distal end. A first portion extends distally from the proximal end and a second portion extends distally from the first portion. A first inflation lumen and an occlusion lumen are formed in the first portion. A second inflation lumen is formed in the second portion. An inflatable proximal balloon is disposed about the first portion and has a balloon wall defining a proximal balloon interior. An inflatable distal balloon is disposed about the second portion and has a balloon wall defining a distal balloon interior. The first and second portions have respective first and second inflation orifices. The first inflation lumen is configured to introduce an inflation fluid into at least one of the balloon interiors by way of the respective inflation orifices. The elongate member has an occlusion port defined between the proximal and distal balloons and the occlusion lumen is configured to introduce an occlusive material into the body cavity by way of the occlusion port.

In a first embodiment, the second lumen is in fluid communication with the first inflation lumen. In this example, the first inflation lumen is configured to introduce the inflation fluid into both of the balloon interiors.

In a second embodiment the elongate member includes an inner wall defining an inner lumen. In one example of this embodiment, the elongate member further includes an elongate inner element extending from the proximal end to the distal end of the elongate member. The inner element is coaxially disposed within the inner lumen for relative axial movement and includes the second portion, the distal balloon, and the second inflation lumen such that the distal balloon may translate axially relative to the proximal balloon. The second inflation lumen is configured to introduce the inflation fluid into the distal balloon interior by way of the second inflation orifice.

In one example of the second embodiment, the second inflation lumen is configured to introduce the inflation fluid into the distal balloon interior independently of the first inflation lumen introducing the inflation fluid into the proximal balloon interior. In another example, the occlusion lumen and the occlusion port are defined in the first portion of the elongate member. In still another example, the inner element includes an element wall defining an element lumen. Other examples may have an atraumatic taper formed at a distal segment of the first portion.

In another embodiment, the occlusive material includes at least one of an adhesive material and small intestine submucosa. The adhesive material may include, for example, at least one of a polyvinyl alcohol and cyanoacrylate.

In still another embodiment, an occlusion device may be disposed about the occlusion port to provide a support structure for the occlusive material. In one example, the occlusion device includes an embolization coil.

In yet another embodiment, a removable film is attached to a distal part of the proximal balloon and a proximal part of the distal balloon. This allows the balloons to be deflated and removed once the occlusive material cures without the balloons attaching to the occlusive material. In still other embodiments, the balloons may be removably attached to the elongate member, allowing the balloons to be permanently left in the body cavity.

The present invention also includes a vascular occlusion assembly for occluding a body cavity. The assembly includes an outer sheath having a proximal section extending to a distal section and defining a sheath lumen therein. Any of the elongate vascular occlusion devices described herein may be disposed within the sheath lumen. The outer sheath is configured to translate axially relative to the elongate occlusion device.

In some examples a wire guide is disposed within an inner lumen of the elongate member. In other examples, the wire guide is disposed within an element lumen of the inner element. In any example, the wire guide is configured such that the elongate occlusion device may translate axially along the wire guide.

The present invention also includes a method of occluding a body. The method includes inserting a wire guide within the body cavity to a desired treatment area and directing an occlusion device along the wire guide to the treatment area. The occlusion device may include any of the devices described herein. The method further includes inflating the proximal and distal balloons with an inflation fluid conveyed through the elongate member to an interior of each of the balloons; contacting the body walls with the inflated balloons; injecting an occlusive material into the body cavity between the balloons; and occluding the body cavity with the occlusive material. In some examples, the body cavity includes a patent foramen ovale of, for example, a human heart.

Further objects, features and advantages of this invention will become readily apparent to persons skilled in the art after a review of the following description, with reference to the drawings and claims that are appended to and form a part of this specification.

DETAILED DESCRIPTION

Figure 1A:
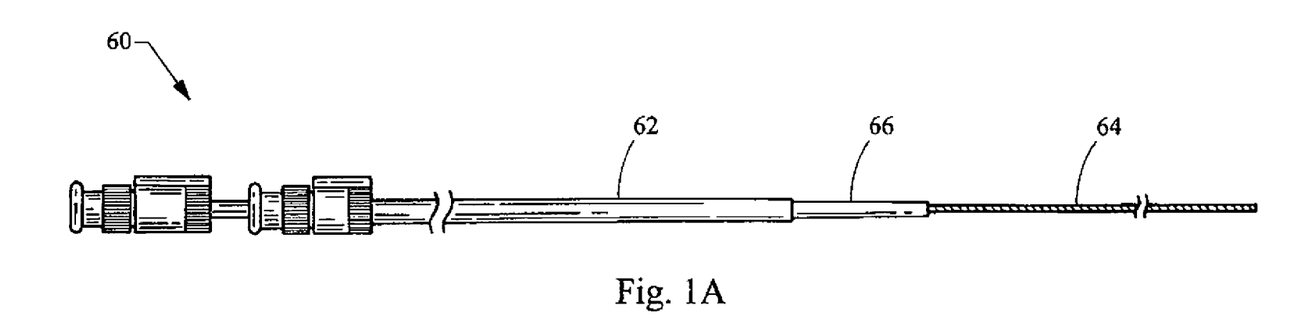
FIG. 1A is a plan view of an occlusion assembly incorporating a vascular occlusion device according to the present invention.
Figure 1B:
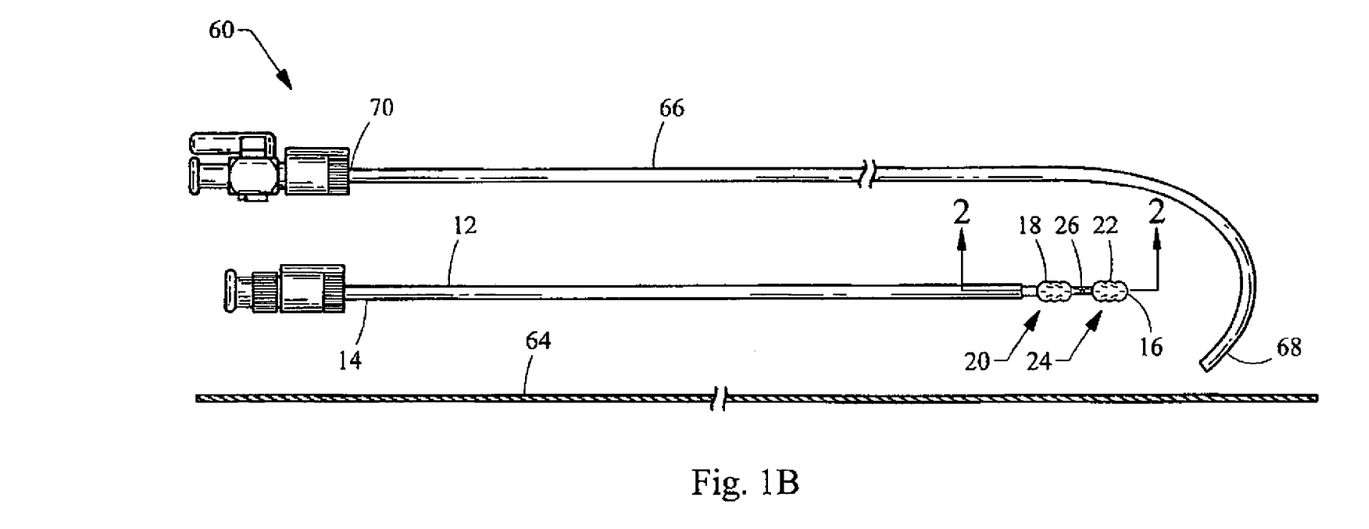
FIG. 1B is an exploded plan view of the occlusion assembly of FIG. 1A.

Referring now to FIG. 1B, a device embodying the principles of the present invention is illustrated therein and designated at 10. As its primary components, the device 10 includes an elongate member 12 extending from a proximal end 14 to a distal end 16. An inflatable proximal balloon 18 is disposed about a first portion 20 of the elongate member 12 and an inflatable distal balloon 22 is disposed about a second portion 24 of the elongate member 12. An occlusion port 26 is defined between the proximal and distal balloons 18 and 22.

Figure 2A:
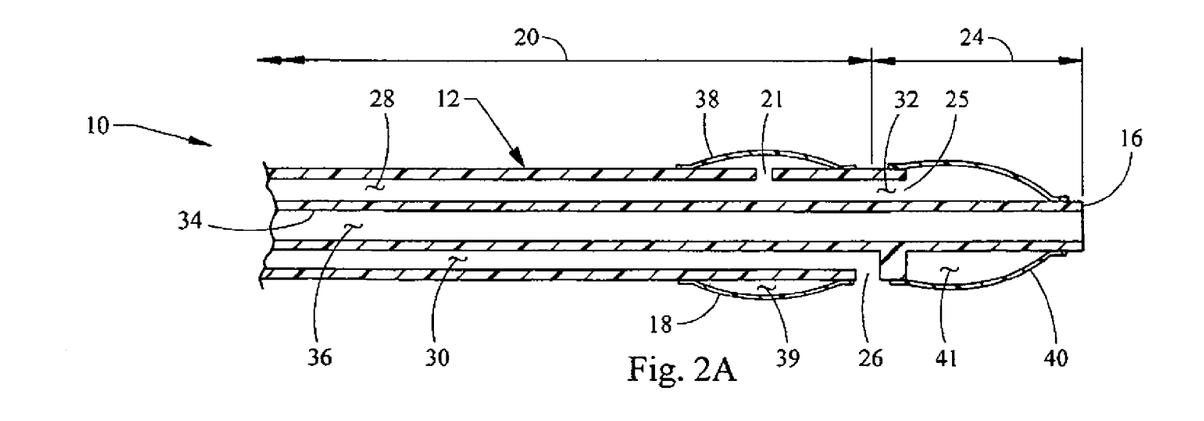
FIG. 2A is a section view through a distal end of one embodiment of the vascular occlusion device of the present invention.

Turning to FIG. 2A a sectional view of one embodiment of the elongate member 12 along line 2-2 of FIG. 1B. As indicated above, the elongate member 12 includes the first portion 20 extending distally from the proximal end 14 and the second portion 24 extending distally from the first portion 20 to the distal end 16. A first inflation lumen 28 and an occlusion lumen 30 are longitudinally formed in the first portion 20. A second inflation lumen 32 is longitudinally formed within the second portion 24. The occlusion port 26 is in fluid communication with the occlusion lumen 30 and is configured to introduce an occlusive material provided from, for example, the proximal end 14 of the elongate member 12, into a body cavity (not shown). In a preferred embodiment, an inner wall 34 defines an inner lumen 36 longitudinally extending through the elongate member 12.

As shown, the proximal and distal balloons 18 and 22 respectively have a proximal balloon wall 38 and a distal balloon wall 40. The balloon walls 38 and 40 are respectively disposed about the circumference of the first and second portions 20 and 24 and respectively define a proximal balloon interior 39 and a distal balloon interior 41. The first and second portions 20 and 24 respectively have a first inflation orifice 21 and a second inflation orifice 25. The first inflation orifice 21 is configured to introduce an inflation fluid provided from, for example, the proximal end 14 of the elongate member 12 through the first inflation lumen 28, into the proximal balloon interior 39 to inflate and expand the proximal balloon 18. In some embodiments, such as that shown in FIG. 2A, the second inflation lumen 32 is in fluid communication with the first inflation lumen 28. In this embodiment, the first inflation lumen 28 will additionally introduce the inflation fluid into the distal balloon interior 41 by way of the second inflation lumen 32 and the second inflation orifice 25. It should be appreciated that while the proximal and distal balloons 18 and 22 are shown as being separate parts attached to the elongate member 12, it is also possible for them to be integrally formed with the elongate member 12.

The elongate member 12 may be made of any appropriate material. Some examples include, but are not limited to, rubber, latex, polytetrafluoroethylene, polyamides, and polyimides.

The inflation fluid may include any appropriate biocompatible fluid for inflating the balloons 18 and 22 and later deflating of the balloons 18 and 22. The occlusive material may include any appropriate biocompatible material having an appropriate viscosity allowing it to flow through the occlusion lumen 30 and occlusion port 26 into the body cavity. In some examples, the occlusive material may be an appropriate adhesive for permanently bonding to body tissue to occlude the body cavity. In other examples, the occlusive material may be configured to promote body tissue growth to occlude the body cavity. Some examples of an adhesive include, but are not limited to, polyvinyl alcohol (PVA) and cyanoacrylate adhesives. An example of a material to promote body tissue growth includes, but is not limited to, extracellular matrix (ECM). In other examples, it may be possible to use a combination of an adhesive and the extracellular matrix to occlude the body cavity.

As known, ECM is a complex structural entity surrounding and supporting cells found within tissues. More specifically, ECM includes structural proteins (for example, collagen and elastin), specialized protein (for example, fibrillin, fibronectin, and laminin), and proteoglycans, a protein core to which are attached long chains of repeating disaccharide units termed glycosaminoglycans.

In a preferred embodiment, the extracellular matrix is comprised of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. SIS may be used to induce site-specific remodeling of both organs and tissues depending on the site of implantation. In practice, host cells are stimulated to proliferate and differentiate into site-specific connective tissue structures, which have been shown to completely replace the SIS material in time.

In this embodiment, SIS may be provided in a fluid form including, for example, a gel. The gel SIS may be used to adhere to walls of the body cavity in which the device 10 is deployed and to promote body tissue growth within the body cavity. SIS has a natural adherence or wetability to body fluids and connective cells comprising the connective tissue of the walls of a body cavity. Since the occlusive material provided by the device 10 is intended to permanently occlude the body cavity, the distal end 16 is positioned such that the SIS may be introduced into contact with host cells of the wall such that the walls will adhere to the SIS and subsequently differentiate, growing into the SIS and eventually occluding the body cavity with the tissue of the walls to which the substance was originally introduced.

Figure 2B:
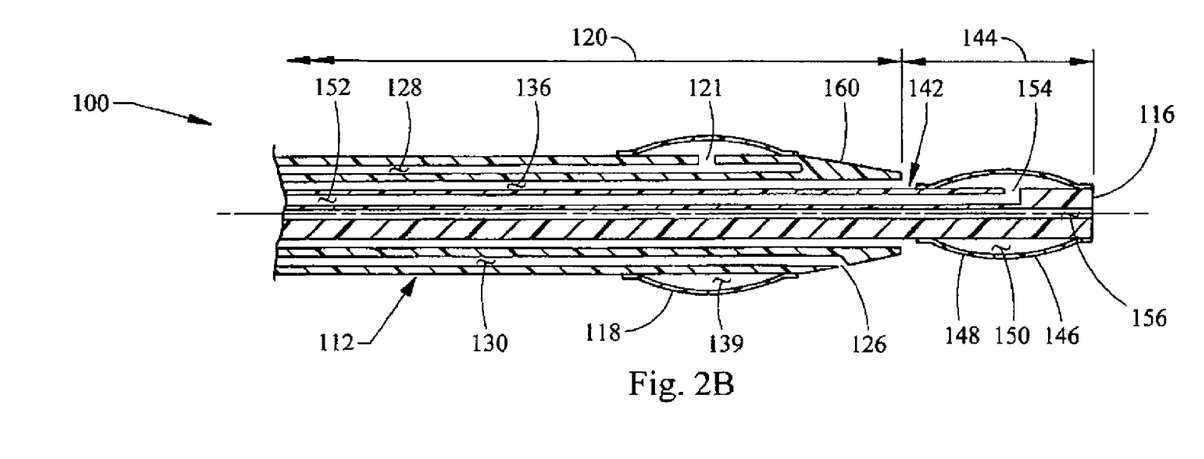
FIG. 2B is a section view through a distal end of another embodiment of the vascular occlusion device of the present invention.

Turning now to FIG. 2B, a sectional view of another embodiment of the present invention is shown. In this embodiment like features to the embodiment of FIG. 2A have like numbers indexed by 100. For example, an elongate member 112 is equivalent to the elongate member 12 and a proximal end 114 of the elongate member 112 is equivalent to the proximal end 14. Other examples include a proximal balloon 118 being equivalent to the proximal balloon 18, an inner lumen 136 being equivalent to the inner lumen 36, and a first portion 120 being equivalent to the first portion 20. However, in this embodiment the elongate member 112 includes an elongate inner element 142 extending from the proximal end 114 to a distal end 116. The inner element 142 includes a second portion 144 extending distally from the first portion 120 and a distal balloon 146 adjacent the distal end 116. The elongate inner element 142 is disposed within the inner lumen 136 for relative axial movement therein such that the distal balloon 146 may translate axially relative to the proximal balloon 118. The distal balloon 146 includes a distal balloon wall 148 disposed about a circumference of a part of the second portion 144, defining a distal balloon interior 150. A second inflation lumen 152 is formed longitudinally within the inner element 142 and is configured to introduce the inflation fluid into the distal balloon interior 150 by way of a second inflation orifice 154.

In one preferred example, the second inflation lumen 152 is configured to introduce the inflation fluid into the distal balloon interior 150 independently of a first inflation lumen 128 introducing the inflation fluid into a proximal balloon interior 139. In a preferred example, the inner element 142 includes an element wall defining an element lumen 156 extending longitudinally therethrough.

In some examples of this embodiment, an occlusion lumen 130 and occlusion port 126 are defined wholly within the first portion 120 of the elongate member 12. In other examples, a distal segment 160 is formed with an atraumatic taper to prevent damage to the body vessel. Similarly, in other examples it is also possible for the distal end 116 to include an atraumatic taper (not shown).

Figure 4A:
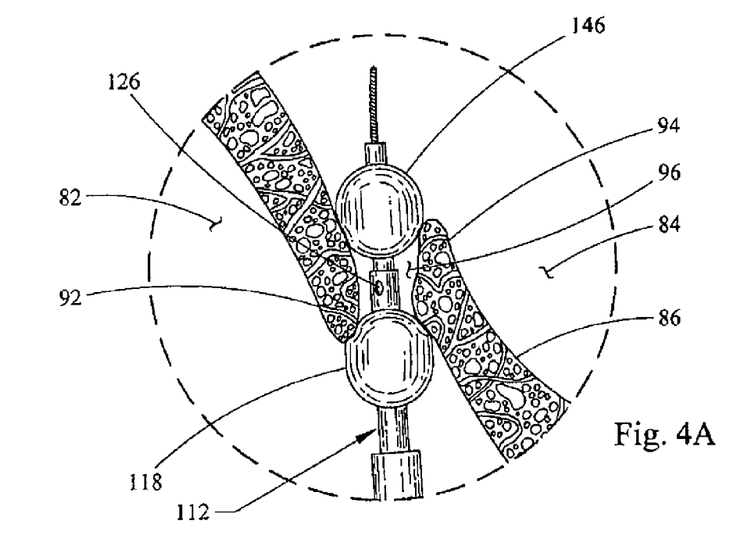
FIGS. 4A-4C show various embodiments of the present invention occluding the patent foramen ovale of FIG. 3.
Figure 4B:
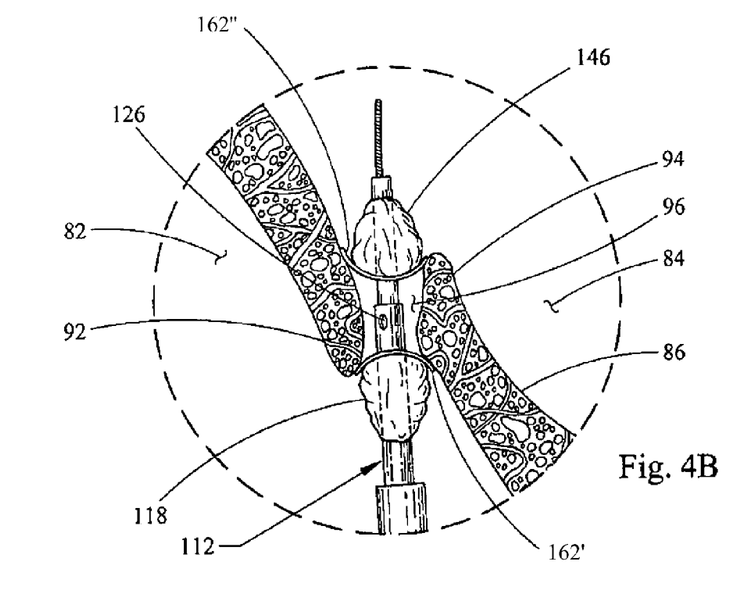
Figure 4C:
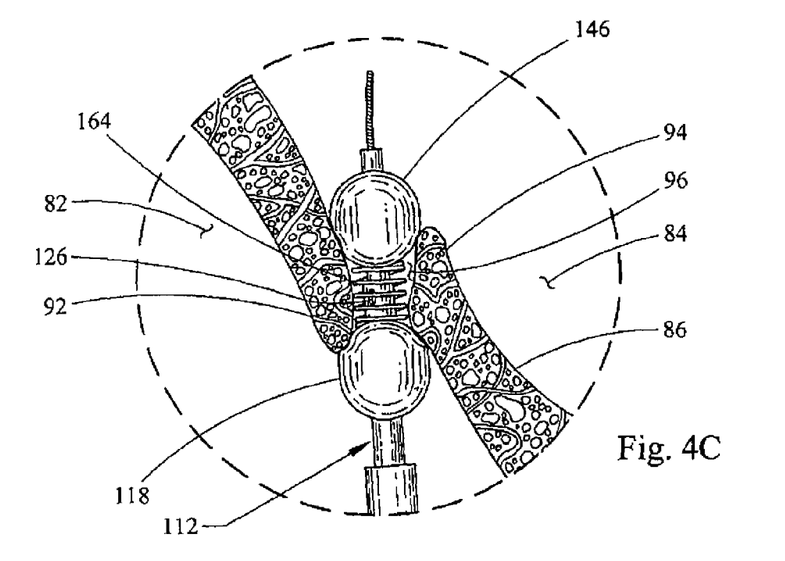

Turning now to FIGS. 4B and 4C, other variations of the present invention are shown. While these drawings show the embodiment of FIG. 2B, these variations also apply equally, but are not limited, to the embodiment of FIG. 2A. In FIG. 4B, a removable film 162 is shown attached to each of the proximal and distal balloons 118 and 146. In the example shown, a first piece of removable film 162' (or a first removable film) is attached to a distal part of the proximal balloon 118 and a second piece of removable film 162" (or a second removable film) is attached to a proximal part of the distal balloon 146. Each piece of removable film 162 is configured to inflate with the balloons 118 and 146, attach to the occlusive material following the introduction of the occlusive material into the body cavity, and detach from the balloons 118 and 146 upon deflation. This allows the elongate member 112 and the balloons 118 and 146 to be withdrawn from the body cavity while leaving the occlusive material in place to occlude the cavity.

In another variation, the proximal and distal balloons 118 and 146 may be detachable from the elongate member 112 (not shown). In this case, the removable film 162 is omitted. As a result, the balloons may be permanently attached to the occlusive material.

In FIG. 4C, an occlusion device 164 is disposed about the occlusion port 126 of the elongate member 112. In this example, the occlusion device 164 is included to provide a support structure upon which the occlusive material may adhere to facilitate occlusion of the body cavity. In some examples, the occlusion device includes, but is not limited to, an embolization coil. One example of an embolization coil includes, but is not limited to, U.S. Pat. No. 5,797,953, which is herein incorporated by reference.

Returning to FIGS. 1A and 1B, a vascular occlusion assembly 60 for introducing and retrieving the vascular occlusion device 10 is shown in accordance with another embodiment of the present invention. As shown, the delivery assembly 60 includes a polytetrafluoroethylene (PTFE) introducer sheath 62 for percutaneously introducing an outer sheath 66 into a body vessel. Of course, any other suitable material for the introducer sheath 62 may be used without falling beyond the scope or spirit of the present invention. The introducer sheath 62 may have any suitable size, for example, between about three-french to eight-french. The introducer sheath 62 serves to allow the outer sheath 66 and the elongate member 12 to be percutaneously inserted to a desired location in a body cavity through the body vessel. For purposes of illustration, only the elongate member 12 is shown, but the elongate member 112 may also be employed. The introducer sheath 62 receives the outer sheath 66 and provides stability to the outer sheath 66 at a desired entry location of the body vessel. For example, the introducer sheath 62 is held stationary within a common visceral artery, and adds stability to the outer sheath 66 as it is advanced through the introducer sheath 62 to an occlusion area in the body cavity.

As shown, the assembly 60 may also include a wire guide 64 configured to be percutaneously inserted within the body vessel to guide the outer sheath 66 to the occlusion area. The wire guide 64 provides the outer sheath 66 with a path to follow as it is advanced within the body vessel. The size of the wire guide 64 is based on an inside diameter of, for example, the inner lumen 32 of the elongate member 12 and the diameter of the body vessels that must be traversed to reach the desired body cavity. When a distal portion 68 of the outer sheath 66 is at the desired location in the body cavity, elongate member 12 is advanced along the wire guide 64 and through the outer sheath 66 to position the distal end 12 and the occlusion port 26 adjacent an area to be occluded within the body cavity, for example, a patent foramen ovale in a human heart.

As shown, the outer sheath 66 also has a proximal portion 70 including a hub 72 to receive the elongate member 12 to be advanced therethrough. The size of the outer sheath 66 is based on the size of the body vessel in which it percutaneously inserts, and the size of the elongate member 12.

Figure 3:
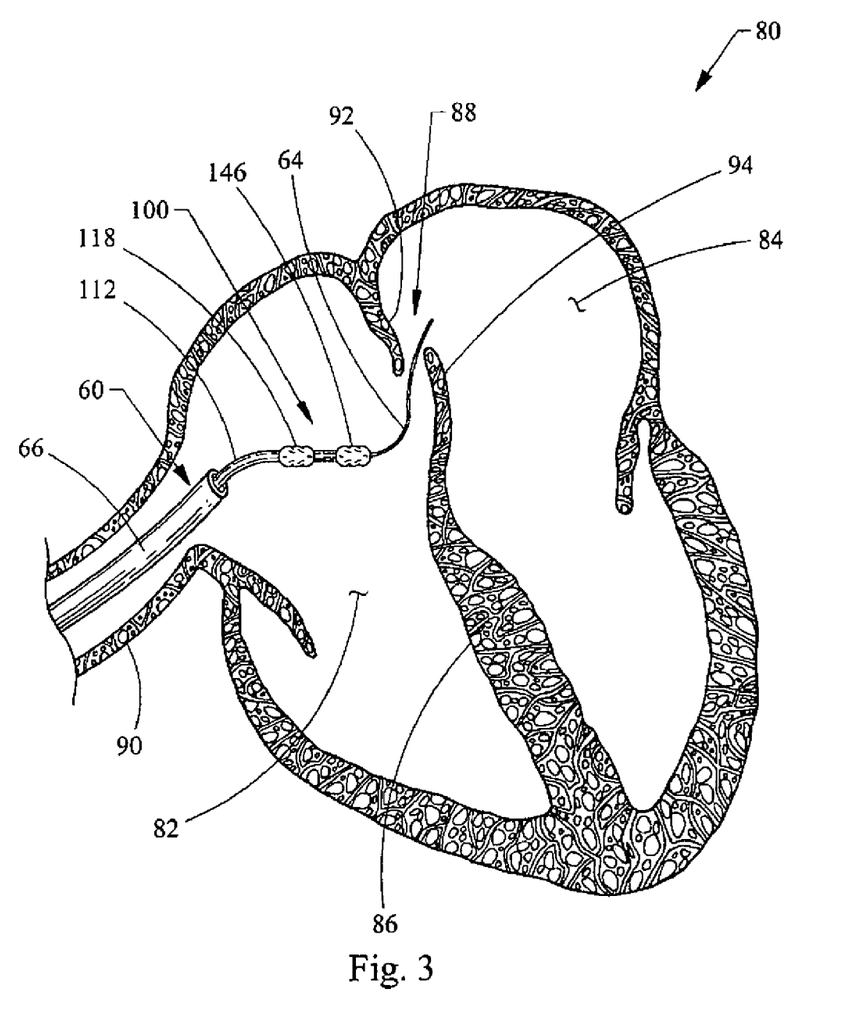
FIG. 3 is a section view of a human heart showing the assembly of FIG. 1A introducing the device of FIG. 2 into a patent foramen ovale.

As mentioned above, one exemplary application of the delivery assembly 60 may be to treat a patent foramen ovale in a human heart 80 as shown in FIGS. 3 and 4A-4C. It should be noted that this is merely one example and the delivery assembly 60 may be used in a variety of other applications to occlude various other body cavities without departing from the scope or spirit of the present invention. FIG. 3 shows a sectional view of the human heart 80 having a right atrium 82 and a left atrium 84. An atrial septum 86 divides the right atrium 82 from the left atrium 84 and defines a patent foramen oval 88. The patent foramen oval 88 is an opening in the atrial septum 86 that allows blood in the right and left atria 82 and 84 to fluidly communicate therebetween.

In a fetus, a foramen ovale is a natural hole in the atrial septum 88 that allows blood to bypass the fetus' lungs when in a mother's womb since the fetus relies on the mother to provide oxygen through the umbilical cord. At birth the foramen ovale normally closes when increased blood pressure in the left atrium forces the opening to close. Over time tissue growth closes the opening permanently. However, in some people the opening does not close permanently, in which case the opening is called a patent foramen ovale.

As shown, the patent foramen ovale 88 acts like a flap valve, having a right flap 92 and a left flap 94, between the two atria 82 and 84. Normally, for example, higher pressure in the left atrium 84 keeps the flaps closed. However, during certain conditions, such as when there is increased pressure inside the chest around the heart, the flaps may open and blood may travel from the right atrium 82 to the left atrium 84. If a clot is present in the right atrium 82 it can, for example, enter the left atrium 84 and travel from there to the brain (causing a stroke) or into a coronary artery (causing a heart attack).

Therefore, it is desirable to close the patent foramen ovale 88 permanently. The delivery assembly 60 may be percutaneously introduced into a body vessel 90 and directed into, for example, the right atrium 82 and maneuvered adjacent the patent foramen ovale 88. The outer sheath 66 is retracted proximally from the occlusion device 100. The wire guide 64 may be directed into the patent foramen ovale 88 to provide a path for the elongate member 112 to follow between the right and left flaps 92 and 94. As best shown in FIG. 4A, the occlusion port 126 is positioned between each of the flaps 92 and 94. The proximal and distal balloons 118 and 146 are inflated into contact with the flaps 92 and 94, thereby forming an occlusion area 96 between the balloons and the flaps (see FIG. 4A). The radial size of the occlusion area 96 may be adjusted, for example, by varying the amount the balloons are inflated. In addition, when using the embodiment of FIG. 2B as shown here, the axial size of the occlusion area 96 may be adjusted by axially translating the inner element 142. The occlusive substance is then introduced to the occlusion area 96 and into contact with the flaps 92 and 94, thereby permanently closing the patent foramen ovale 88.

Figure 5:
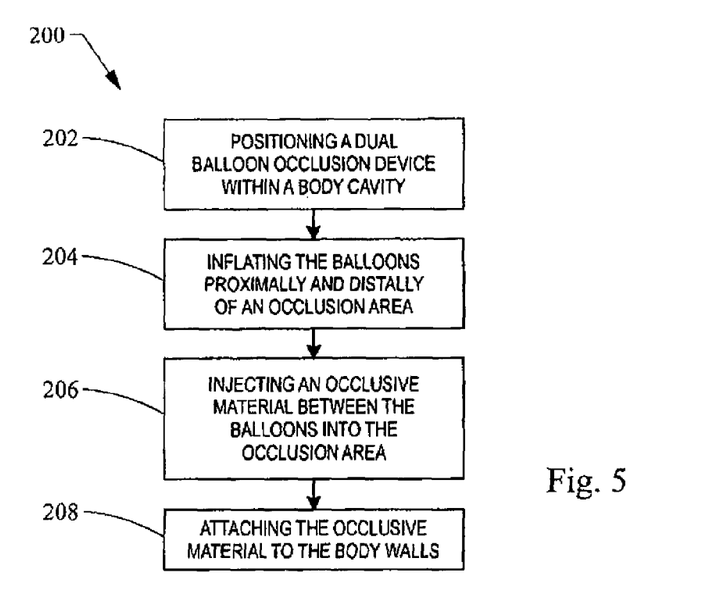
FIG. 5 is a flow chart illustrating a method of occluding a body cavity.

FIG. 5 is a flow chart illustrating a method 200 of occluding a body cavity. The method 200 includes at box 202 positioning any of the occlusion devices described herein within a body cavity. Box 204 includes inflating balloons of the occlusion device proximally and distally of an occlusion area within the body cavity. Box 206 includes introducing an occlusive material between the balloons and into the occlusion area, and box 208 attaches the occlusive material to the body walls of the body cavity.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

I claim:

1. A vascular occlusion device for occluding a body cavity defined by cavity walls, the device comprising:
   an elongate member extending from a proximal end to a distal end and including a first portion extending distally from the proximal end and a second portion extending distally from the first portion to the distal end, a first inflation lumen and an occlusion lumen being formed longitudinally in the first portion, and a second inflation lumen being formed longitudinally in the second portion;
   an occlusive material configured to permanently occlude the body cavity disposed within the occlusion lumen, the occlusive material including extracellular matrix (ECM);
   an inflatable proximal balloon including a proximal balloon wall being disposed about the first portion and defining a proximal balloon interior;
   an inflatable distal balloon including a distal balloon wall being disposed about the second portion and defining a distal balloon interior;
   the first and second portions respectively having first and second inflation orifices, the first inflation lumen being configured to introduce an inflation fluid into at least one of the balloon interiors by way of the respective inflation orifices; and
   the elongate member having an occlusion port defined between the proximal and distal balloons, the occlusion lumen being configured to introduce the occlusive material into the body cavity by way of the occlusion port to occlude the body cavity;
   wherein a first removable film is attached to a distal part of the proximal balloon and a second removable film is attached to a proximal part of the distal balloon, the removable films being configured to inflate with the balloons, attach to the occlusive material following introduction of the occlusive material into the body cavity, and detach from the balloons upon deflation of the balloons.

2. The device of claim 1 wherein the second inflation lumen is in fluid communication with the first inflation lumen, the first inflation lumen being configured to introduce the inflation fluid into each of the balloon interiors by way of the respective inflation orifices and the second inflation lumen.

3. The device of claim 1 wherein the elongate member further comprises an inner wall defining an inner lumen extending through the distal end of the elongate member.

4. The device of claim 1 wherein the occlusive material further includes at least one of a polyvinyl alcohol and a cyanoacrylate, and the extracellular matrix (ECM) includes small intestine submucosa.

5. The device of claim 1 wherein an occlusion device is disposed about the occlusion port to provide a support structure for the occlusive material.

6. The device of claim 5 wherein the occlusion device includes an embolization coil.

7. The device of claim 1 wherein the balloons are removably attached to the elongate member.

8. A vascular occlusion assembly for occluding a body cavity defined by cavity walls, the assembly comprising:
   an outer sheath having a proximal section extending to a distal section and defining a sheath lumen therein, an elongate vascular occlusion device being disposed within the sheath lumen and the outer sheath being configured to translate axially relative to the elongate occlusion device;
   the occlusion device comprising an elongate member extending from a proximal end to a distal end and including a first portion extending distally from the proximal end, a second portion extending distally from the first portion to the distal end, a first inflation lumen and an occlusion lumen being formed longitudinally in the first portion, a second inflation lumen being formed longitudinally in the second portion, and an inner wall defining an inner lumen extending longitudinally through the elongate member, the inner lumen extending through the distal end of the elongate member;
   an occlusive material configured to permanently occlude the body cavity disposed within the occlusion lumen, the occlusive material including extracellular matrix (ECM);
   an inflatable proximal balloon including a proximal balloon wall being disposed about the first portion and defining a proximal balloon interior;
   an inflatable distal balloon including a distal balloon wall being disposed about the second portion and defining a distal balloon interior;
   the first and second portions respectively having first and second inflation orifices, the first inflation lumen being configured to introduce an inflation fluid into at least one of the balloon interiors by way of the respective inflation orifices; and
   the elongate member having an occlusion port defined between the proximal and distal balloons, the occlusion lumen being configured to introduce the occlusive material into the body cavity by way of the occlusion port; and a longitudinally extending wire guide being disposed within the inner lumen and configured such that the elongate occlusion device may translate axially along the wire guide;

wherein a first removable film is attached to a distal part of the proximal balloon and a second removable film is attached to a proximal part of the distal balloon, the removable films being configured to inflate with the balloons, attach to the occlusive material following introduction of the occlusive material into the body cavity, and detach from the balloons upon deflation of the balloons.

9. The device of claim 8 wherein the second inflation lumen is in fluid communication with the first inflation lumen, the first inflation lumen being configured to introduce the inflation fluid into each of the balloon interiors by way of the respective inflation orifices and the second inflation lumen.

10. The device of claim 8 wherein the occlusive material further includes at least one of a polyvinyl alcohol and a cyanoacrylate, and the extracellular matrix includes small intestine submucosa.

11. The device of claim 1 wherein the extracellular matrix (ECM) includes small intestine submucosa provided in a gel form.

12. A vascular occlusion device for occluding a body cavity defined by cavity walls, the device comprising:

an elongate member extending from a proximal end to a distal end and including a first portion extending distally from the proximal end and a second portion extending distally from the first portion to the distal end, a first inflation lumen and an occlusion lumen being formed longitudinally in the first portion, and a second inflation lumen being formed longitudinally in the second portion;

an occlusive material configured to permanently occlude the body cavity disposed within the occlusion lumen, the occlusive material including extracellular matrix (ECM);

an inflatable proximal balloon including a proximal balloon wall being disposed about the first portion and defining a proximal balloon interior;

an inflatable distal balloon including a distal balloon wall being disposed about the second portion and defining a distal balloon interior;

the first and second portions respectively having first and second inflation orifices, the first inflation lumen being configured to introduce an inflation fluid into at least one of the balloon interiors by way of the respective inflation orifices; and the elongate member having an occlusion port defined between the proximal and distal balloons, the occlusion lumen being configured to introduce the occlusive material into the body cavity by way of the occlusion port to occlude the body cavity, wherein the second inflation lumen is in fluid communication with the first inflation lumen, the first inflation lumen being configured to introduce the inflation fluid into each of the balloon interiors by way of the respective inflation orifices and the second inflation lumen, and wherein the inflatable proximal balloon and the inflatable distal balloon are disposed adjacent to each other about the elongate member with no intervening inflatable balloons disposed therebetween;

wherein a first removable film is attached to a distal part of the proximal balloon and a second removable film is attached to a proximal part of the distal balloon, the removable films being configured to inflate with the balloons, attach to the occlusive material following introduction of the occlusive material into the body cavity, and detach from the balloons upon deflation of the balloons.

13. The device of claim 12, the inflatable proximal and distal balloons being integrally formed with the elongate member.

14. The device of claim 13 wherein the extracellular matrix (ECM) includes small intestine submucosa provided in a gel form.

15. A vascular occlusion device for occluding a body cavity defined by cavity walls, the device comprising:

an elongate member extending from a proximal end to a distal end and including a first portion extending distally from the proximal end and a second portion extending distally from the first portion to the distal end, a first inflation lumen and an occlusion lumen being formed longitudinally in the first portion, and a second inflation lumen being formed longitudinally in the second portion;

an inflatable proximal balloon including a proximal balloon wall being disposed about the first portion and defining a proximal balloon interior;

an inflatable distal balloon including a distal balloon wall being disposed about the second portion and defining a distal balloon interior;

the first and second portions respectively having first and second inflation orifices, the first inflation lumen being configured to introduce an inflation fluid into at least one of the balloon interiors by way of the respective inflation orifices; and the elongate member having an occlusion port defined between the proximal and distal balloons, the occlusion lumen being configured to introduce an occlusive material into the body cavity by way of the occlusion port to occlude the body cavity;

wherein a first removable film is attached to a distal part of the proximal balloon and a second removable film is attached to a proximal part of the distal balloon, the removable films being configured to inflate with the balloons, attach to the occlusive material following introduction of the occlusive material into the body cavity, and detach from the balloons upon deflation of the balloons.

* * * * *

UNITED STATES PATENT AND TRADEMARK OFFICE
CERTIFICATE OF CORRECTION

| | |
|---|---|
| PATENT NO. | : 8,292,907 B2 |
| APPLICATION NO. | : 11/848777 |
| DATED | : October 23, 2012 |
| INVENTOR(S) | : Michael R. Kurrus |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1087 days.

Signed and Sealed this
Twenty-first Day of October, 2014

Michelle K. Lee
*Deputy Director of the United States Patent and Trademark Office*